(12) United States Patent
Shin et al.

(10) Patent No.: US 11,419,574 B2
(45) Date of Patent: Aug. 23, 2022

(54) ULTRASOUND IMAGING APPARATUS, METHOD OF CONTROLLING THE SAME, AND COMPUTER PROGRAM PRODUCT

(71) Applicant: SAMSUNG MEDISON CO., LTD., Hongcheon-gun (KR)

(72) Inventors: Dongkuk Shin, Seongnam-si (KR); Hyunjae Jeon, Seongnam-si (KR)

(73) Assignee: SAMSUNG MEDISON CO., LTD., Hongcheon-gun (KR)

(*) Notice: Subject to any disclaimer, the term of this patent is extended or adjusted under 35 U.S.C. 154(b) by 111 days.

(21) Appl. No.: 16/811,854

(22) Filed: Mar. 6, 2020

(65) Prior Publication Data

US 2020/0281560 A1 Sep. 10, 2020

(30) Foreign Application Priority Data

Mar. 8, 2019 (KR) .................. 10-2019-0027016

(51) Int. Cl.
*A61B 8/08* (2006.01)
*A61B 8/06* (2006.01)
(Continued)

(52) U.S. Cl.
CPC ............ *A61B 8/085* (2013.01); *A61B 8/06* (2013.01); *A61B 8/0858* (2013.01); *A61B 8/14* (2013.01);
(Continued)

(58) Field of Classification Search
CPC ......... A61B 8/085; A61B 8/06; A61B 8/0858; A61B 8/14; A61B 8/463; A61B 8/483;
(Continued)

(56) References Cited

U.S. PATENT DOCUMENTS

| 8,208,989 B2 | 6/2012 | Maschke et al. |
| 9,144,421 B1 | 9/2015 | Lau et al. |

(Continued)

FOREIGN PATENT DOCUMENTS

| JP | 2007-159924 A | 6/2008 |
| JP | 2009-285315 A | 12/2009 |

(Continued)

OTHER PUBLICATIONS

Revelli et al., Ultrasound Obstet Gynecol, 2016; 48: 289-295, DOI: 10.1002/uog.15899.*

(Continued)

*Primary Examiner* — Bo Joseph Peng
(74) *Attorney, Agent, or Firm* — Sughrue Mion, PLLC

(57) ABSTRACT

An ultrasound imaging apparatus includes: a probe configured to transmit ultrasound waves and detect echo signals; a display; and at least one processor configured to generate an ultrasound image based on the echo signals, wherein the at least one processor is further configured to obtain a three-dimensional (3D) medical image of a uterus, determine a target position for embryo transfer based on the 3D medical image, obtain a real-time ultrasound image of the uterus, identify the target position in the real-time ultrasound image, and control the display to display the real-time ultrasound image and information about the target position.

9 Claims, 13 Drawing Sheets

(51) Int. Cl.
*A61B 8/14* (2006.01)
*A61B 8/00* (2006.01)

(52) U.S. Cl.
CPC .............. *A61B 8/463* (2013.01); *A61B 8/483* (2013.01); *A61B 8/5223* (2013.01); *A61B 8/4405* (2013.01); *A61B 2562/0219* (2013.01)

(58) Field of Classification Search
CPC ................ A61B 8/5223; A61B 8/4405; A61B 2562/0219; A61B 8/0866; A61B 8/5246; A61B 8/4444; A61B 8/5207; A61B 8/54
See application file for complete search history.

(56) References Cited

U.S. PATENT DOCUMENTS

| | | |
|---|---|---|
| 9,452,050 B2 | 9/2016 | Miles et al. |
| 2005/0261546 A1 | 11/2005 | Gergely |
| 2012/0179040 A1* | 7/2012 | Arai .................. A61B 8/463 600/443 |
| 2014/0160114 A1* | 6/2014 | Stevenson ............. A61B 8/488 345/419 |
| 2015/0294497 A1* | 10/2015 | Ng ..................... A61B 8/466 382/128 |
| 2016/0166233 A1 | 6/2016 | Yoo et al. |
| 2016/0242740 A1 | 8/2016 | Day |
| 2016/0278688 A1 | 9/2016 | Pierzynski et al. |
| 2017/0340354 A1 | 11/2017 | Gilson et al. |
| 2018/0035915 A1 | 2/2018 | Babu |
| 2019/0147022 A1 | 5/2019 | Okada |
| 2019/0247022 A1 | 8/2019 | Lee et al. |

FOREIGN PATENT DOCUMENTS

| | | |
|---|---|---|
| JP | 4863799 B2 | 1/2012 |
| JP | 2014-516594 A | 7/2014 |
| JP | 2016-154858 A | 9/2016 |
| JP | 2017-507764 A | 3/2017 |
| KR | 10-2012-0122542 A | 1/2012 |
| KR | 10-2012-0122542 A | 11/2012 |
| KR | 10-1473192 B1 | 12/2014 |
| KR | 10-2016-0073168 A | 6/2016 |
| KR | 10-1652641 B1 | 9/2016 |
| KR | 10-1876643 B1 | 7/2018 |
| WO | 2010/096419 A2 | 8/2010 |
| WO | 2010/096419 A3 | 8/2010 |
| WO | 2018/222006 A1 | 12/2018 |

OTHER PUBLICATIONS

Gergely et al., "Three dimensional/four dimensional ultrasound-guided embryo transfer using the maximal implantation potential point", Fertility and Sterility, vol. 84, No. 2, doi:10.1016/j.fertnstert 2005.01.141, Aug. 2005, pp. 500-503, 4 pages total, XP027697706.
Communication dated Jul. 28, 2020 issued by the European Intellectual Property Office in counterpart European Application No. 20158802.7.

* cited by examiner

ULTRASOUND IMAGING APPARATUS, METHOD OF CONTROLLING THE SAME, AND COMPUTER PROGRAM PRODUCT

CROSS-REFERENCE TO RELATED APPLICATION(S)

This application is based on and claims priority under 35 U.S.C. § 119 to Korean Patent Application No. 10-2019-0027016, filed on Mar. 8, 2019, in the Korean Intellectual Property Office, the disclosure of which is incorporated by reference herein in its entirety.

BACKGROUND

1. Field

The disclosure relates to ultrasound imaging apparatuses, methods of controlling the same, and computer program products.

2. Description of Related Art

Ultrasound imaging apparatuses transmit ultrasound signals generated by transducers of a probe to an object and receive information about signals reflected from the object, thereby obtaining at least one ultrasound image of an internal part, for example, soft tissue or blood flow, of the object. Ultrasound imaging apparatuses are capable of obtaining medical images in real-time. Due to this, such ultrasound imaging apparatuses have been widely used to obtain real-time images during medical procedures or surgeries.

SUMMARY

Provided are ultrasound imaging apparatuses and methods of controlling the same, which are capable of increasing a success rate of embryo transfer to the uterus.

Provided are also ultrasound imaging apparatuses and methods of controlling the same, which are capable of increasing user convenience and providing a guide to the user during embryo transfer to the uterus.

Additional aspects will be set forth in part in the description which follows and, in part, will be apparent from the description, or may be learned by practice of the presented embodiments.

In accordance with an aspect of the disclosure, an ultrasound imaging apparatus includes: a probe configured to transmit ultrasound waves and detect echo signals; a display; and at least one processor configured to generate an ultrasound image based on the echo signals, wherein the at least one processor is further configured to obtain a three-dimensional (3D) medical image of a uterus, determine a target position for embryo transfer based on the 3D medical image, obtain a real-time ultrasound image of the uterus, identify the target position in the real-time ultrasound image, and control the display to display the real-time ultrasound image and information about the target position.

the at least one processor may be further configured to acquire a value of at least one parameter based on the 3D medical image, determine the target position based on the value of the at least one parameter, match the value of the at least one parameter acquired based on the 3D medical image to the real-time ultrasound image, and control the display to display information about the value of the at least one parameter in the real-time ultrasound image.

The at least one parameter may include at least one of an endometrial thickness, a blood flow amount, a junction zone location, a uterine boundary location, an endometrial location, a myoma location, and an adenomyoma location, or a combination thereof.

The probe may include at least one sensor including at least one of a position sensor, a gyro sensor, and an accelerometer, and the at least one processor may be further configured to register the 3D medical image with the real-time ultrasound image based on a signal detected by the at least one sensor.

The at least one processor may be further configured to provide information about a position of the real-time ultrasound image on the 3D medical image.

The 3D medical image and the real-time ultrasound image may be respectively obtained by apparatuses using different imaging modalities The at least one processor may be further configured to provide, based on the 3D medical image, information about the probability of successful implantation at a position of at least a portion of the uterus.

The at least one processor may be further configured to provide information about a distance between a plane corresponding to the real-time ultrasound image and the target position.

The least one processor may be further configured to provide a guide for moving the probe to obtain the real-time ultrasound image corresponding to the target position.

The real-time ultrasound image may show at least one procedure tool inserted into the uterus, and the at least one processor may be further configured to control the display to display the 3D medical image and the real-time ultrasound image and provide, on the 3D ultrasound image, information about a position of the at least one procedure tool detected in the real-time ultrasound image.

The real-time ultrasound image may correspond to a real-time two-dimensional (2D) ultrasound image or a real-time 3D ultrasound image.

In accordance with another aspect of the disclosure, a method of controlling an ultrasound imaging apparatus includes: obtaining a 3D medical image of a uterus; determining a target position for embryo transfer based on the 3D medical image; obtaining a real-time ultrasound image of the uterus; identifying the target position in the real-time ultrasound image; and displaying the real-time ultrasound image and information about the target position.

In accordance with another aspect of the disclosure, a computer program is stored on a recording medium and includes at least one instruction that, when executed by a processor, performs a method of controlling an ultrasound imaging apparatus, the method including: obtaining a 3D medical image of a uterus; determining a target position for embryo transfer based on the 3D medical image; obtaining a real-time ultrasound image of the uterus; identifying the target position in the real-time ultrasound image; and displaying the real-time ultrasound image and information about the target position.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
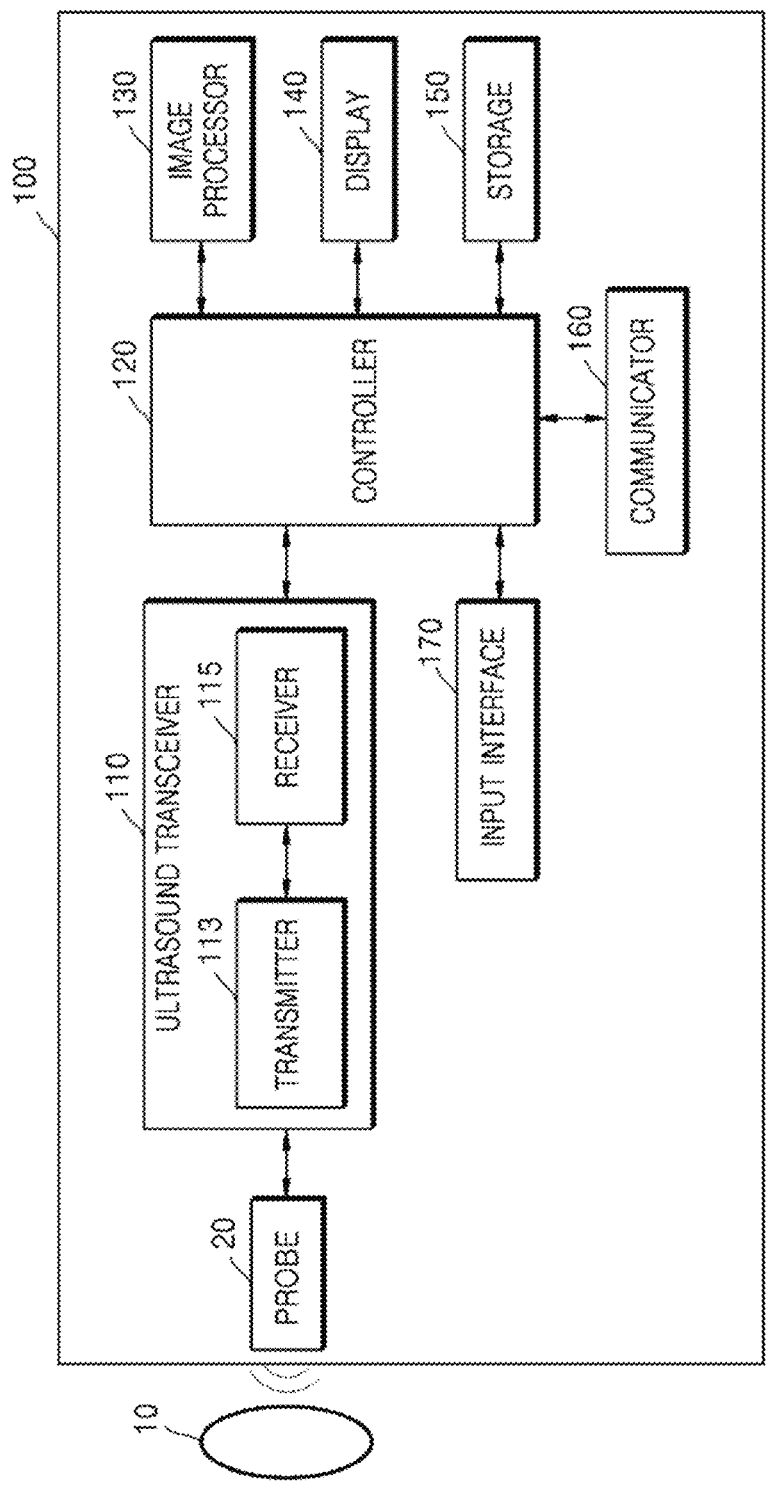
FIG. 1 is a block diagram illustrating an ultrasound diagnosis apparatus according to an exemplary embodiment.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

Terms such as "part" and "portion" used herein denote those that may be embodied by software or hardware. According to exemplary embodiments, a plurality of parts or portions may be embodied by a single unit or element, or a single part or portion may include a plurality of elements.

In exemplary embodiments, an image may include any medical image acquired by various medical imaging apparatuses such as a magnetic resonance imaging (MRI) apparatus, a computed tomography (CT) apparatus, an ultrasound imaging apparatus, or an X-ray apparatus.

Also, in the present specification, an "object", which is a thing to be imaged, may include a human, an animal, or a part thereof. For example, an object may include a part of a human, that is, an organ or a tissue, or a phantom.

Throughout the specification, an ultrasound image refers to an image of an object processed based on ultrasound signals transmitted to the object and reflected therefrom.

As used herein, the term "and/or" includes any and all combinations of one or more of the associated listed items. Expressions such as "at least one of," when preceding a list of elements, modify the entire list of elements and do not modify the individual elements of the list.

FIG. 1 is a block diagram illustrating a configuration of an ultrasound diagnosis apparatus 100, i.e., a diagnostic apparatus, according to an exemplary embodiment.

Referring to FIG. 1, the ultrasound diagnosis apparatus 100 may include a probe 20, an ultrasound transceiver 110, a controller 120, an image processor 130, one or more displays 140, a storage 150, e.g., a memory, a communicator 160, i.e., a communication device or an interface, and an input interface 170.

The ultrasound diagnosis apparatus 100 may be of a cart-type or a portable-type ultrasound diagnosis apparatus, which is portable, moveable, mobile, or hand-held. Examples of the ultrasound diagnosis apparatus 100 of a portable type may include a smart phone, a laptop computer, a personal digital assistant (PDA), and a tablet personal computer (PC), each of which may include a probe and a software application, but embodiments are not limited thereto.

The probe 20 may include a plurality of transducers. The plurality of transducers may transmit ultrasound signals to an object 10 in response to transmitting signals received by the probe 20, from a transmitter 113. The plurality of transducers may receive ultrasound signals reflected from the object 10 to generate reception signals. In addition, the probe 20 and the ultrasound diagnosis apparatus 100 may be formed in one body (e.g., disposed in a single housing), or the probe 20 and the ultrasound diagnosis apparatus 100 may be formed separately (e.g., disposed separately in separate housings) but linked wirelessly or via wires. In addition, the ultrasound diagnosis apparatus 100 may include one or more probes 20 according to embodiments.

The controller 120 may control the transmitter 113 for the transmitter 113 to generate transmitting signals to be applied to each of the plurality of transducers based on a position and a focal point of the plurality of transducers included in the probe 20.

The controller 120 may control an ultrasound receiver 115 to generate ultrasound data by converting reception signals received from the probe 20 from analog to digital signals and summing the reception signals converted into digital signals, based on a position and a focal point of the plurality of transducers.

The image processor 130 may generate an ultrasound image by using ultrasound data generated from the ultrasound receiver 115.

The display 140 may display a generated ultrasound image and various pieces of information processed by the ultrasound diagnosis apparatus 100. The ultrasound diagnosis apparatus 100 may include two or more displays 140 according to the present exemplary embodiment. The display 140 may include a touch screen in combination with a touch panel.

The controller 120 may control the operations of the ultrasound diagnosis apparatus 100 and flow of signals between the internal elements of the ultrasound diagnosis apparatus 100. The controller 120 may include a memory for storing a program or data to perform functions of the ultrasound diagnosis apparatus 100 and a processor and/or a microprocessor (not shown) for processing the program or data. For example, the controller 120 may control the operation of the ultrasound diagnosis apparatus 100 by receiving a control signal from the input interface 170 or an external apparatus.

The ultrasound diagnosis apparatus 100 may include the communicator 160 and may be connected to external apparatuses, for example, servers, medical apparatuses, and portable devices such as smart phones, tablet personal computers (PCs), wearable devices, etc., via the communicator 160.

The communicator 160 may include at least one element capable of communicating with the external apparatuses. For example, the communicator 160 may include at least one of a short-range communication module, a wired communication module, and a wireless communication module.

The communicator 160 may receive a control signal and data from an external apparatus and transmit the received control signal to the controller 120 so that the controller 120 may control the ultrasound diagnosis apparatus 100 in response to the received control signal.

The controller 120 may transmit a control signal to the external apparatus via the communicator 160 so that the external apparatus may be controlled in response to the control signal of the controller 120.

For example, the external apparatus connected to the ultrasound diagnosis apparatus 100 may process the data of the external apparatus in response to the control signal of the controller 120, received via the communicator 160.

A program for controlling the ultrasound diagnosis apparatus 100 may be installed in the external apparatus. The program may include instructions to perform part of operation of the controller 120 or the entire operation of the controller 120.

The program may be pre-installed in the external apparatus or may be installed by a user of the external apparatus by downloading the program from a server that provides applications. The server that provides applications may include a recording medium where the program is stored.

The storage 150 may store various data or programs for driving and controlling the ultrasound diagnosis apparatus 100, input and/or output ultrasound data, ultrasound images, applications, etc.

The input interface 170 may receive a user's input to control the ultrasound diagnosis apparatus 100 and may include a keyboard, button, keypad, mouse, trackball, jog switch, knob, a touchpad, a touch screen, a microphone, a motion input means, a biometrics input means, etc. For example, the user's input may include inputs for manipulating buttons, keypads, mice, trackballs, jog switches, or knobs, inputs for touching a touchpad or a touch screen, a voice input, a motion input, and a bioinformation input, for example, iris recognition or fingerprint recognition, but an exemplary embodiment is not limited thereto.

An example of the ultrasound diagnosis apparatus 100 according to the present exemplary embodiment is described below with reference to FIGS. 2A, 2B, and 2C.

Figure 2A:
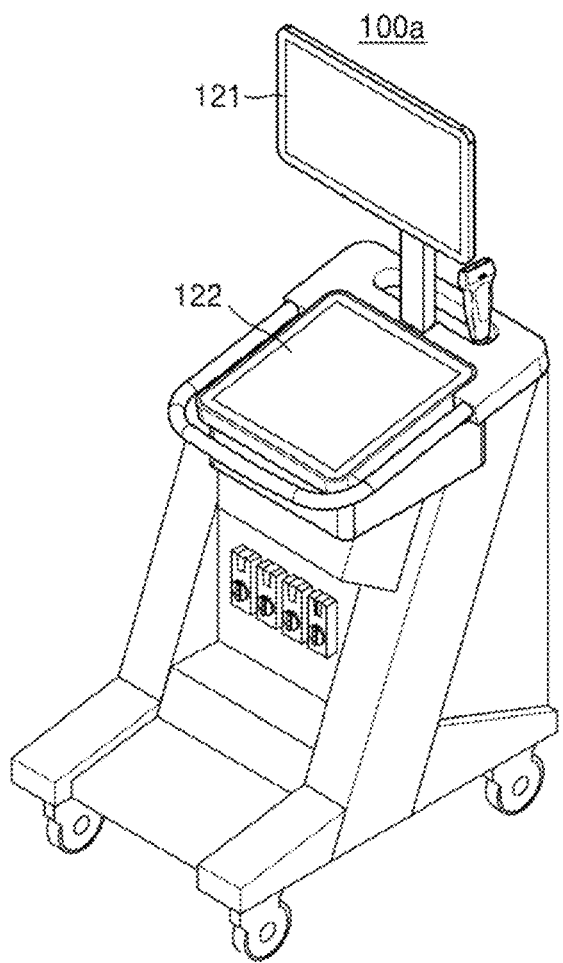
FIGS. 2A, 2B, and 2C are diagrams respectively illustrating an ultrasound diagnosis apparatus according to an exemplary embodiment.
Figure 2B:
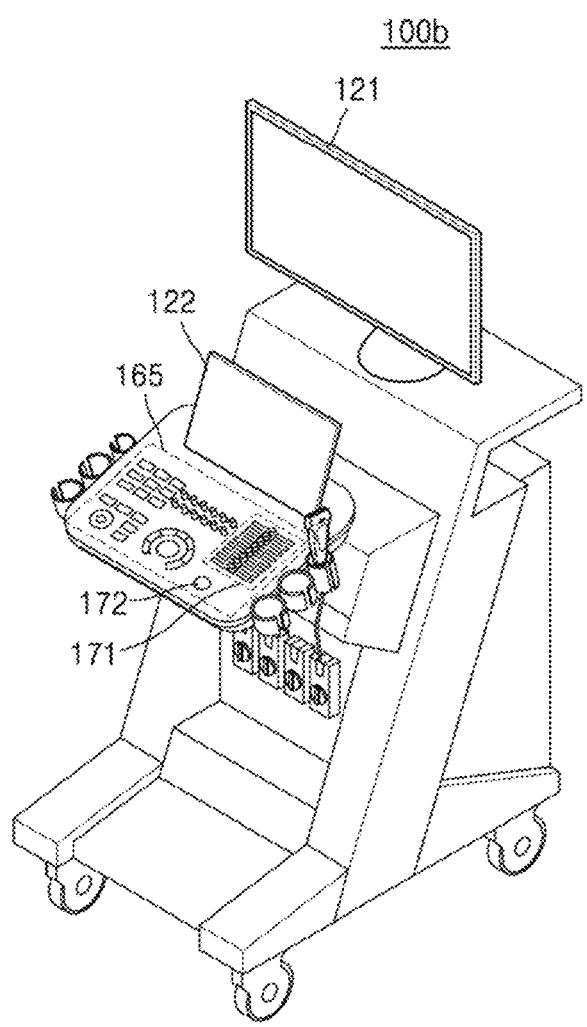
Figure 2C:
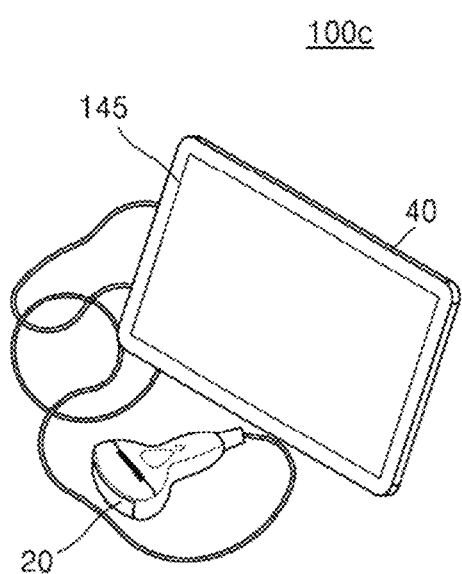

FIGS. 2A, 2B, and 2C are diagrams illustrating ultrasound diagnosis apparatuses according to an exemplary embodiment.

Referring to FIGS. 2A and 2B, the ultrasound diagnosis apparatus 100a or 100b may include a main display 121 and a sub-display 122. At least one of the main display 121 and the sub-display 122 may include a touch screen. The main display 121 and the sub-display 122 may display ultrasound images and/or various information processed by the ultrasound diagnosis apparatus 100a or 100b. The main display 121 and the sub-display 122 may provide graphical user interfaces (GUIs), thereby receiving user's inputs of data to control the ultrasound diagnosis apparatus 100a or 100b. For example, the main display 121 may display an ultrasound image and the sub-display 122 may display a control panel to control display of the ultrasound image as a GUI. The sub-display 122 may receive an input of data to control the display of an image through the control panel displayed as a GUI. The ultrasound diagnosis apparatus 100a or 100b may control the display of the ultrasound image on the main display 121 by using the input control data.

Referring to FIG. 2B, the ultrasound diagnosis apparatus 100b may include a control panel 165. The control panel 165 may include buttons, trackballs, jog switches, or knobs and may receive data to control the ultrasound diagnosis apparatus 100b from the user. For example, the control panel 165 may include a time gain compensation (TGC) button 171 and a freeze button 172. The TGC button 171 is to set a TGC value for each depth of an ultrasound image. Also, when an input of the freeze button 172 is detected during scanning of an ultrasound image, the ultrasound diagnosis apparatus 100b may keep displaying a frame image at that time point.

The buttons, trackballs, jog switches, and knobs included in the control panel 165 may be provided as a GUI to the main display 121 or the sub-display 122.

Referring to FIG. 2C, an ultrasound diagnosis apparatus 100c may include a portable device. An example of the ultrasound diagnosis apparatus 100c of a portable type may include, for example, smart phones including probes and applications, laptop computers, personal digital assistants (PDAs), or tablet PCs, but an exemplary embodiment is not limited thereto.

The ultrasound diagnosis apparatus 100c may include the probe 20 and a main body 40. The probe 20 may be connected to one side of the main body 40 by wire or wirelessly. The main body 40 may include a touch screen 145. The touch screen 145 may display an ultrasound image, various pieces of information processed by the ultrasound diagnosis apparatus 100c, and a GUI.

Figure 3:
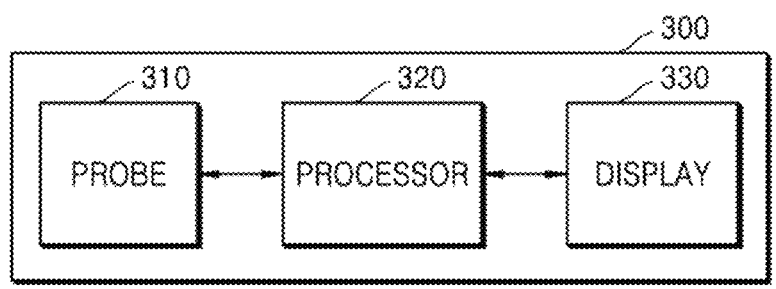
FIG. 3 is a block diagram of a structure of an ultrasound imaging apparatus according to an embodiment.

FIG. 3 is a block diagram of a structure of an ultrasound imaging apparatus 300 according to an embodiment.

According to an embodiment, the ultrasound imaging apparatus 300 includes a probe 310, a processor 320, and a display 330.

The probe 310 includes a plurality of transducers and transmits ultrasound signals to an object and detects echo signals reflected from the object. The probe 310 may correspond to the probe 20 of FIG. 1.

The processor 320 controls all operations of the ultrasound imaging apparatus 300. The processor 320 may be implemented as one or more processors. The processor 320 receives ultrasound signals from the probe 310 to reconstruct an ultrasound image. Ultrasound signals generated by the probe 310 undergo predetermined signal processing through a beamformer, an amplifier, an analog-to-digital converter (ADC), etc., and are then transmitted to the processor 320. The processor 320 may execute an instruction or command stored in a memory to perform a specific operation.

The display 330 displays ultrasound images and predetermined data. The display 330 displays a GUI view provided by the ultrasound imaging apparatus 300. The display 330 may correspond to the display 140 of FIG. 1.

Figure 4:
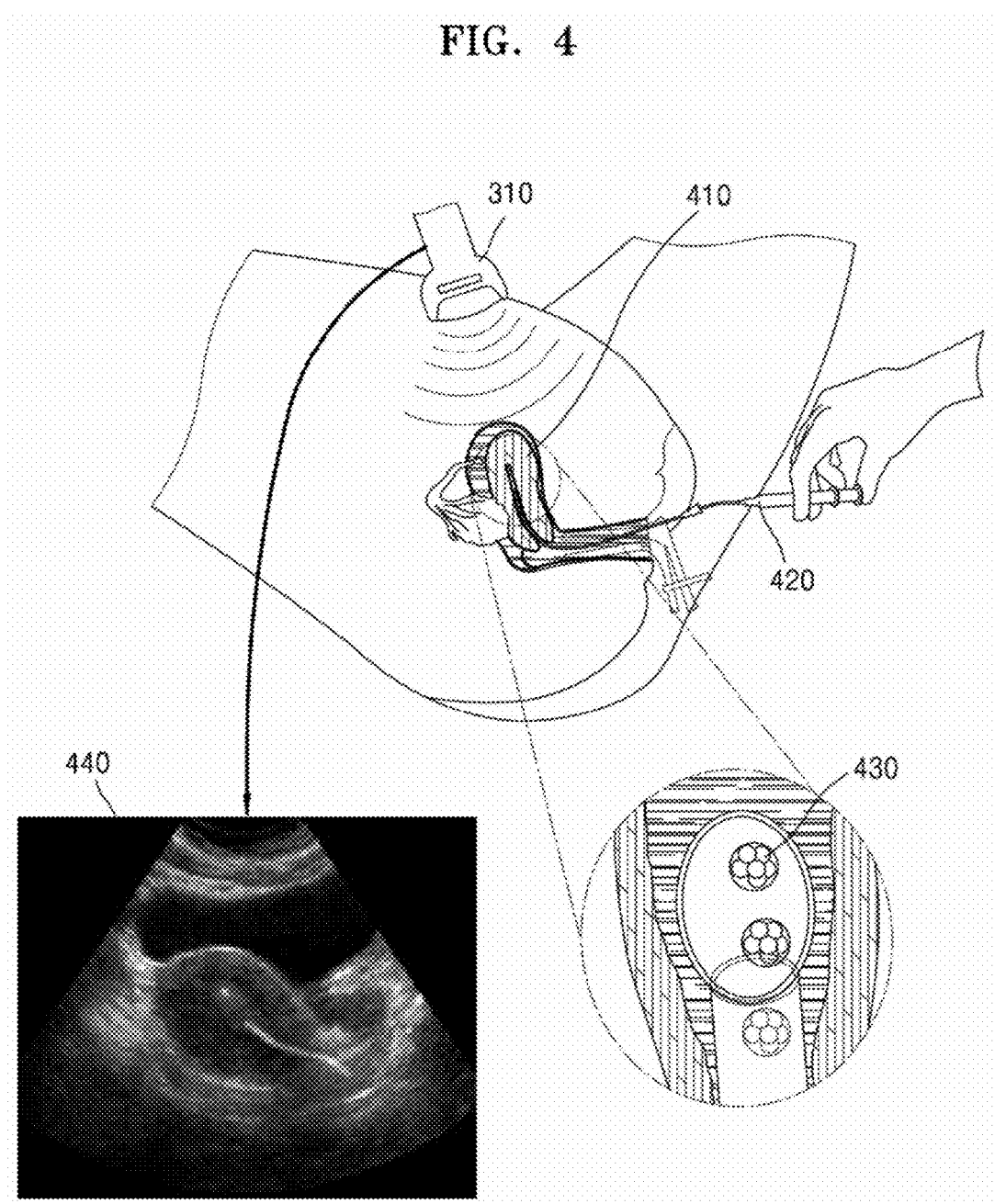
FIG. 4 is a diagram for explaining a process of transferring an embryo to the uterus, according to an embodiment.

FIG. 4 is a diagram for explaining a process of transferring an embryo to the uterus, according to an embodiment.

An embryo transfer procedure for transferring an embryo 430 to a uterus 410 has been widely used for in vitro fertilization (IVF). Real-time medical images are necessarily required to protect a patient during embryo transfer and improve a success rate of the embryo transfer. Ultrasound imaging is widely used in medical procedures because it may offer medical images of an object in real-time.

During an embryo transfer procedure, a procedure tool 420 containing the embryo 430 is inserted into a patient's body, and the embryo 430 in the procedure tool 420 is then transferred to a proper position in the uterus 410. To increase a success rate of embryo transfer, it is critical to transfer the embryo 430 to the proper position in the uterus 410. To find the proper position in the uterus 410 for embryo transfer, the medical personnel captures an image of a region of the uterus 410 via the probe 310 to examine a real-time medical image 440.

However, because an ultrasound image obtained as a real-time medical image is usually a two-dimensional (2D) ultrasound image, there is a limitation in acquiring information about a three-dimensional (3D) structure within the uterus. Furthermore, when only a 2D ultrasound image is used, there is a limitation that parameters obtainable from a 3D medical image cannot be utilized.

According to embodiments of the disclosure, an embryo transfer process may include determining a target position for embryo transfer by using a 3D medical image of the uterus 410, identifying the target position in a real-time ultrasound image, and displaying information about the target position on the display 330. Thus, a success rate of transfer of the embryo 430 to the uterus 410 may be increased.

According to embodiments of the disclosure, the real-time medical image 440 may be a 2D or 3D ultrasound image. Although embodiments of the disclosure are described herein with respect to an example in which the real-time medical image 440 is a 2D ultrasound image, the scope of the present application is not limited thereto.

Figure 5:
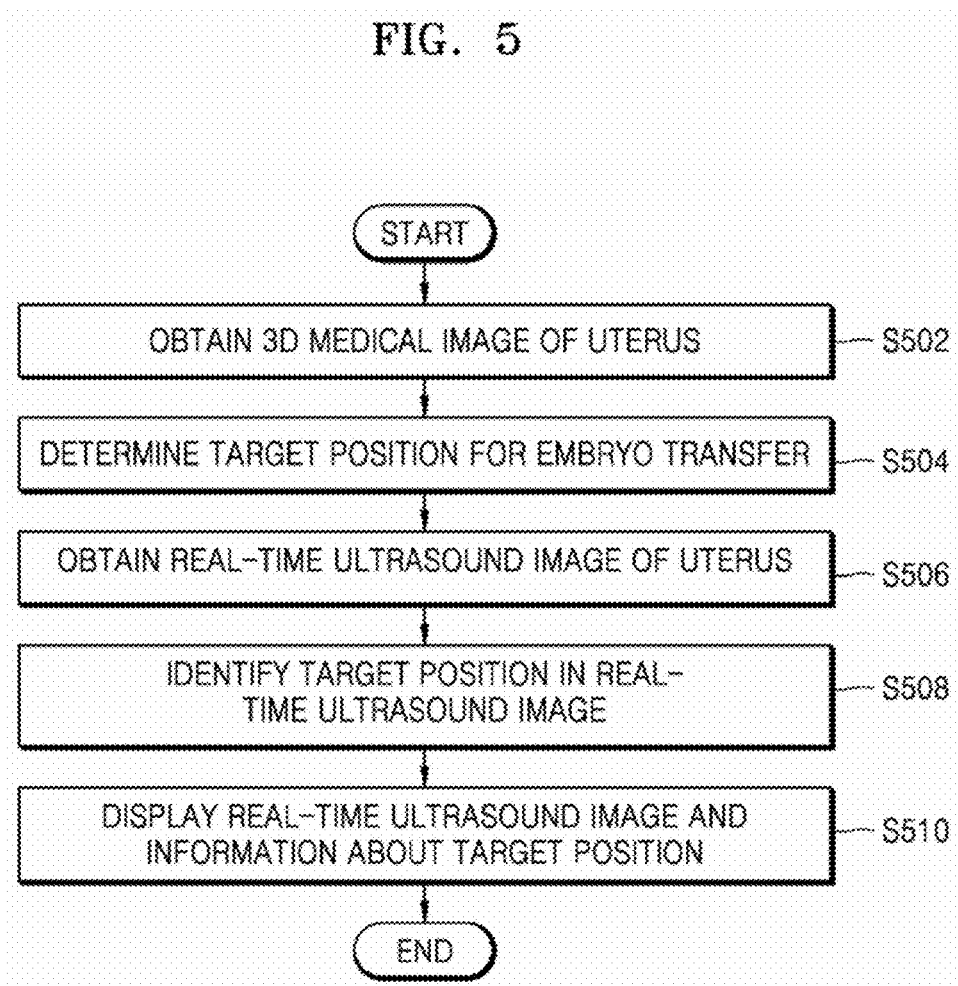
FIG. 5 is a flowchart of a method of controlling an ultrasound imaging apparatus, according to an embodiment.

FIG. 5 is a flowchart of a method of controlling an ultrasound imaging apparatus, according to an embodiment.

Operations of a method of controlling an ultrasound imaging apparatus according to the disclosure may be performed by an ultrasound imaging apparatus including a probe and a processor. The disclosure will be described with respect to an embodiment in which the ultrasound imaging apparatus 300 performs a method of controlling an ultrasound imaging apparatus. 300 is hereinafter used as a reference numeral collectively denoting ultrasound imaging apparatuses according to embodiments of the disclosure. Thus, embodiments described with respect to the ultrasound imaging apparatus 300 may be applied to a method of controlling the ultrasound imaging apparatus 300. Conversely, embodiments described with respect to a method of controlling the ultrasound imaging apparatus 300 may be applied to embodiments described with respect to the ultrasound imaging apparatus 300. Although it has been described that methods of controlling an ultrasound imaging apparatus according to embodiments of the disclosure are performed by the ultrasound imaging apparatus 300, embodiments are not limited thereto, and the methods may be performed by various types of ultrasound imaging apparatus.

Referring to FIG. 5, first, the ultrasound imaging apparatus 300 obtains a 3D medical image of the uterus (S502). The ultrasound imaging apparatus 300 may include a memory storing 3D medical images.

According to an embodiment, the ultrasound imaging apparatus 300 obtains a 3D medical image of the uterus from an external apparatus. According to an embodiment, the 3D medical image may be an ultrasound image. According to another embodiment, the 3D medical image may be a medical image of a different imaging modality than ultrasound, such as a CT or MR image. The ultrasound imaging apparatus 300 may include a communicator via which a 3D medical image is obtained from an external apparatus. The ultrasound imaging apparatus 300 may provide a mode for acquiring a 3D medical image obtained from an external apparatus, a mode for loading the 3D medical image, etc.

According to another embodiment, the ultrasound imaging apparatus 300 may obtain a 3D ultrasound image of the uterus via the probe 310. According to an embodiment, a 3D ultrasound image and a 2D ultrasound image may be obtained using different types of the probe 310. For this purpose, a 3D probe and a 2D probe may be respectively used to acquire a 3D ultrasound image and a 2D ultrasound image. According to another embodiment, the ultrasound imaging apparatus 300 may acquire both 3D and 2D ultrasound images via a single probe. In this case, the probe 310 may be a probe for performing both 3D and 2D imaging, and for example, may correspond to a 3D vaginal probe, a 2D matrix probe, etc. The ultrasound imaging apparatus 300 may provide an imaging process and a mode for sequentially performing 3D imaging and 2D imaging.

According to an embodiment, a 3D medical image and a real-time ultrasound image may be obtained using a probe capable of performing 3D imaging. The real-time ultrasound image may correspond to a 3D ultrasound image. For example, a 3D medical image and a real-time 3D ultrasound image may be obtained using a 2D matrix probe.

Next, the processor 320 determines a target position for embryo transfer by using the 3D medical image (S504).

The processor 320 recognizes an anatomical structure of the uterus in the 3D ultrasound image. For example, the processor 320 recognizes in the 3D medical image an anatomical structure such as an ovary, a fallopian tube, an endometrium, a perimetrium, a junction zone, etc. For recognition, predetermined segmentation may be performed on the 3D medical image.

Furthermore, the processor 320 extracts parameter values related to embryo transfer from the 3D medical image. Parameter values related to embryo transfer may include at least one of a maximal implantation potential (MIP) point, an endometrial thickness, a blood flow amount, a junction zone location, a uterine shape, an implantation location, a uterine location, an endometrial location, and a location of a lesion (e.g., myoma or adenomyoma), or a combination thereof. At least one parameter value related to embryo transfer may be calculated in a 3D space. Furthermore, at least one parameter value may be determined for each position in the 3D space. For example, at least one parameter value may be matched to at least some coordinates in the 3D space or to each coordinate therein. A map representing a parameter value in the 3D space may be generated for a specific parameter value corresponding to at least some positions or coordinates in the 3D space.

A target position for embryo transfer may be determined based on at least one of an anatomical structure of the uterus and at least one parameter value related to the embryo transfer or a combination thereof. The processor 320 may determine a target position for embryo transfer where a success rate of embryo transfer is high, based on at least one of an anatomical structure of the uterus and at least one parameter value related to embryo transfer. The target position may be determined as a specific point or region. The target position may be determined in the 3D space within the uterus.

Then, the processor 320 obtains a real-time ultrasound image of the uterus by using the probe 310 (S506).

The processor 320 matches the real-time ultrasound image that is a 2D ultrasound image to the target position and at least one parameter value acquired based on the 3D ultrasound image. The processor 320 may register the 2D ultrasound image with the 3D medical image to identify the target position in the 2D ultrasound image and match at least one parameter value to the 2D ultrasound image.

Various techniques may be used for registration between the 2D ultrasound image and the 3D medical image.

According to an embodiment, the processor 320 may register the 2D ultrasound image with the 3D medical image by using image registration. For example, the processor 320 may perform image registration by using anatomical features or by matching edges in the 2D ultrasound image with edges in the 3D medical image.

According to another embodiment, the processor 320 may register the 2D ultrasound image with the 3D medical image by using a detection value detected by a sensor. For example, the probe 310 may include a position sensor for detecting a position of the probe 310, an accelerometer or gyro sensor for detecting its orientation, or a combination thereof. The processor 320 may identify a plane corresponding to the 2D ultrasound image in the 3D medical image by using position information or orientation information detected by the sensor and may match the 2D ultrasound image to the plane identified in the 3D medical image.

Subsequently, the processor 320 displays on the display 330 the real-time ultrasound image and information about the target position (S510). The target position may be displayed in the 2D ultrasound image. According to an embodiment, the processor 320 may display a 2D ultrasound image and information about the target position on a GUI view, together with at least one parameter value.

Furthermore, the processor 320 may recognize a procedure tool in the 2D ultrasound image and provide a guide for moving the procedure tool to the target position based on a position of the procedure tool. For example, the processor 320 may provide information about the position of the procedure tool or information about how to move the procedure tool to the target position.

When the real-time ultrasound image does not correspond to a plane where the target position is located, the processor 320 may provide a guide for moving the probe 310 to image the plane corresponding to the target position.

As the procedure tool moves, the processor 320 may update a guide for movement of the procedure tool and a guide for movement of the probe 310.

Figure 6:
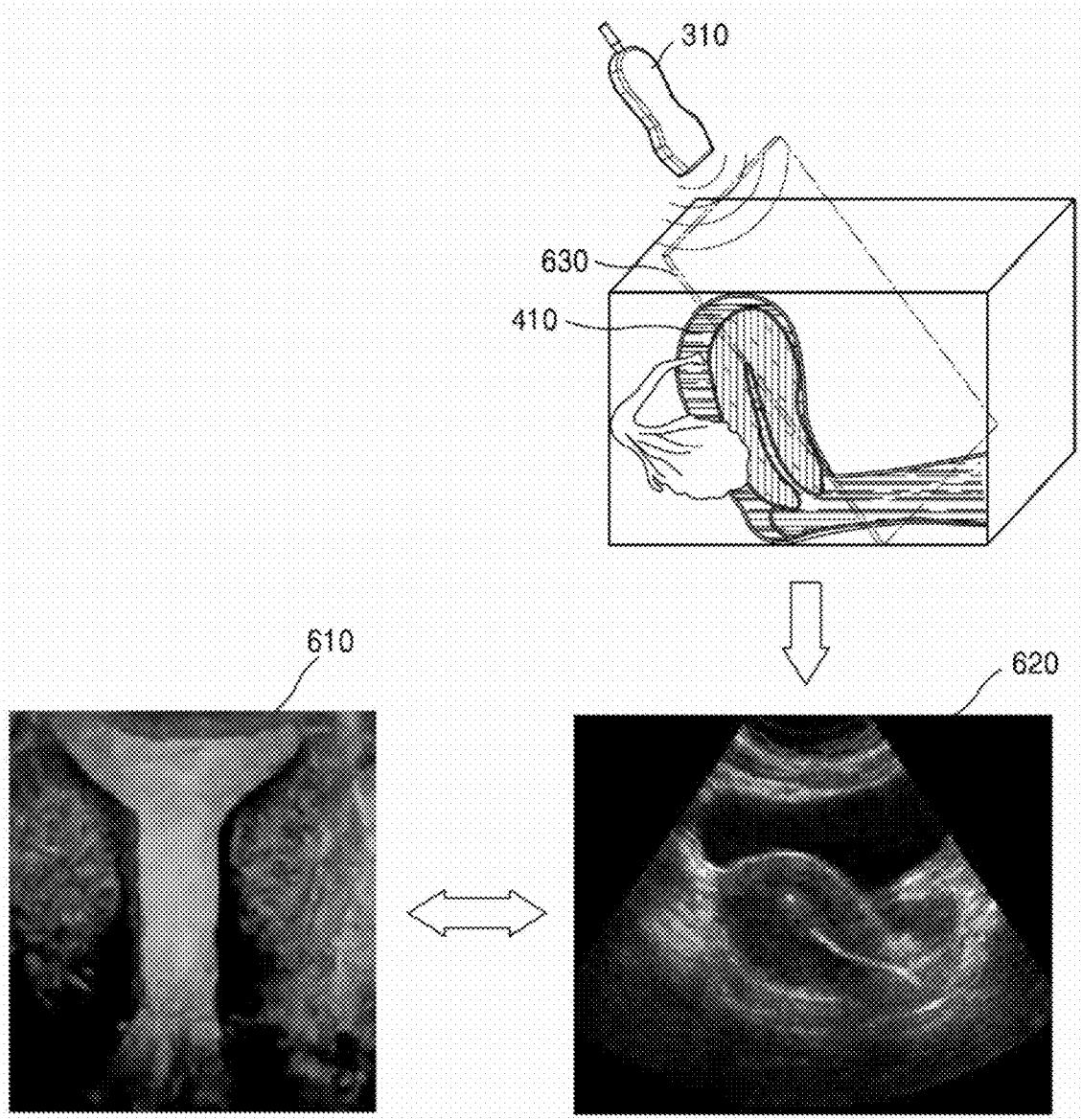
FIG. 6 illustrates a three-dimensional (3D) medical image and a two-dimensional (2D) ultrasound image according to an embodiment.

FIG. 6 illustrates a 3D medical image 610 and a 2D ultrasound image 620 according to an embodiment.

The 3D medical image 610 and the 2D ultrasound image 620 are captured images of the same patient's uterus 410. The 3D medical image 610 and the 2D ultrasound image may be captured at adjacent time points. For example, the 3D medical image 610 and the 2D ultrasound image 620 may be captured on the same day.

The 2D ultrasound image 620 may correspond to a predetermined plane 630 in a 3D space. The predetermined plane 630 corresponding to the 2D ultrasound image 620 may change in real-time according to movement of the probe 310. According to an embodiment, the ultrasound imaging apparatus 300 may provide the 2D ultrasound image 620 together with a position of the probe 310 in the 3D space and information about the predetermined plane 630 corresponding to the 2D ultrasound image 620.

Figure 7:
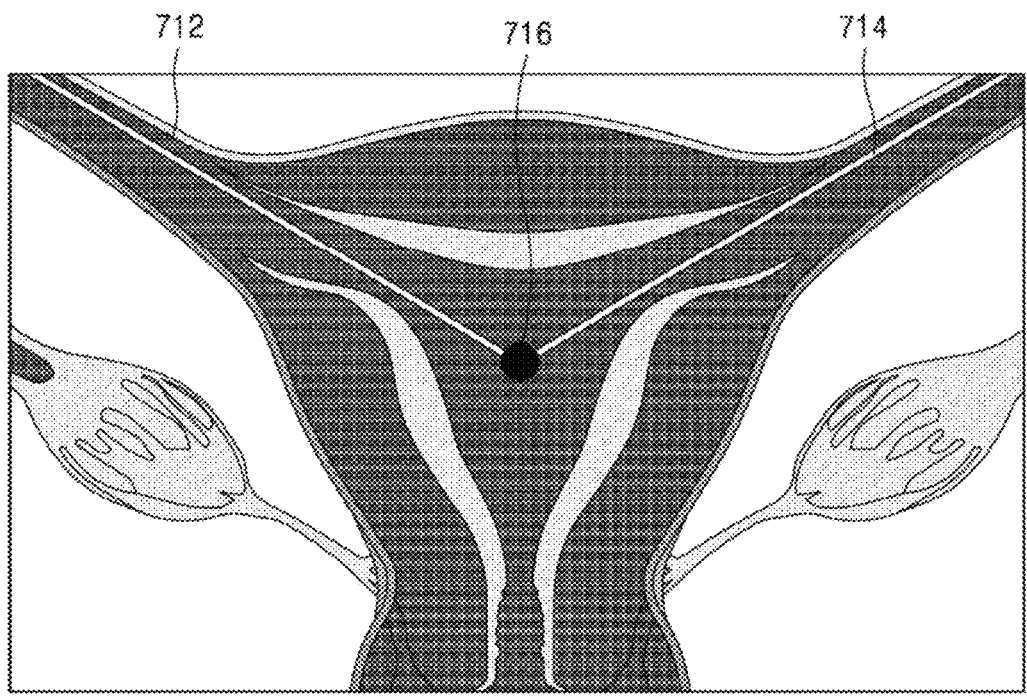
FIG. 7 illustrates a maximum implantation potential (MIP) point according to an embodiment.

FIG. 7 illustrates an MIP point according to an embodiment.

A target position for embryo transfer may be determined based on at least one of an anatomical structure of the uterus and at least one parameter value related to the embryo transfer or a combination thereof. The processor 320 may create, based on the anatomical structure of the uterus and the at least one parameter value, a 3D transfer probability map showing a good position for transfer and store the 3D transfer probability map. At least one parameter may include an endometrial thickness, a blood flow amount, a junction zone location, a uterine shape, an implantation location, a uterine location, an endometrial location, an MIP point, a uterine morphological pattern, etc.

A score indicating a good position for embryo implantation is hereinafter referred to as an implantation score. An implantation score is a value representing an implantation success rate.

The processor 320 may score a good position for embryo implantation according to an endometrial thickness. For example, when the endometrial thickness does not exceed 7 mm, an implantation success rate decreases.

The processor 320 may determine an implantation score according to the amount of blood flow. The processor 320 may determine an implantation score based on the amount of blood flow in an angiography image. As the amount of blood flow increases, an implantation success rate is considered to be higher.

The processor 320 may determine an implantation score according to a thickness, a sharpness, and contraction/relaxation extent of a junction zone. As the junction zone has a more uniform thickness, the probability of successful implantation is considered to be higher. As the junction zone is connected more smoothly without being cut off, the probability of successful implantation is considered to be higher.

The processor 320 may determine an implantation score based on uterine contraction and relaxation When there is no uterine contraction, an implantation success rate is considered to be higher. Furthermore, when uterine contraction and relaxation are to a smaller extent, the probability of successful implantation is considered to be higher.

The processor 320 may determine an implantation score according to a uterine shape and an implantation location. An optimal position for implantation may be in a triangular region at the center of the uterus, and the processor 320 may determine an implantation score according to whether a location for implantation is within the triangular region The triangular region at the center of the uterus is determined as an MIP point 716. According to an embodiment, a point where lines 712 and 714 connected along two uterine tubes intersect each other is determined as the MIP point 716, and use of the MIP point 716 or a predetermined region including the MIP point 716 is considered to achieve a high probability of successful implantation.

The processor 320 may determine an implantation score according to a morphological pattern of the uterus. Homogeneity of a morphological pattern may indicate a high probability that adenomyoma or myoma exists in the uterus, and an implantation success rate may decrease due to the presence of such a lesion.

By applying an implantation score determined based on a plurality of parameter values to a predetermined equation, the processor 320 may obtain an evaluation value indicating an implantation success rate based on a resultant value obtained using the equation. The evaluation value may be calculated according to a position in the uterus. The evaluation value may be calculated in various forms such as a final implantation success rate, a final implantation score, etc.

The processor 320 may create a 3D transfer probability map by mapping an evaluation value determined as described above according to a position in the uterus and store the 3D transfer probability map. The 3D transfer probability map may be displayed on 2D or 3D image data based on an evaluation value. The 3D transfer probability map may represent an evaluation value at each position in the uterus by using graphical indicators such as a color, a graph, etc.

Figure 8:
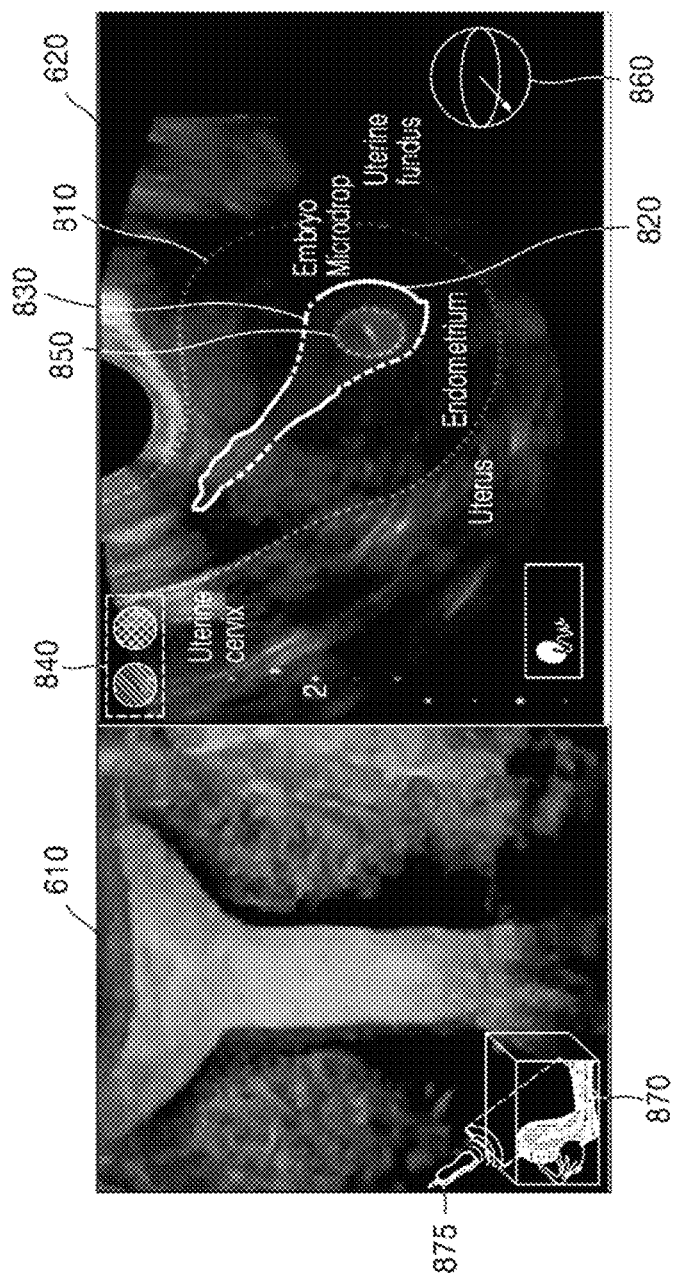
FIG. 8 illustrates a graphical user interface (GUI) view according to an embodiment.

FIG. 8 illustrates a GUI view according to an embodiment.

According to an embodiment, the processor 320 may display on the display 330 a GUI view that provides both a 3D medical image 610 and a 2D ultrasound image 620.

According to an embodiment, the GUI view may provide a first indicator 870 showing a position in a 3D space corresponding to the 2D ultrasound image 620. The first indicator 870 may be provided together with a second indicator (875) indicating the probe 310. The first indicator 870 may be updated in response to a change in a position of the probe 310. The processor 320 may calculate a position in the 3D space corresponding to the 2D ultrasound image 620 according to movement of the probe 310 and update the first indicator 870 based on the calculated position in the 3D space.

According to an embodiment, the GUI view may show a uterine boundary 810 in the 2D ultrasound image 620. The uterine boundary 810 refers to an outer boundary of the uterus. According to an embodiment, the processor 320 may automatically recognize and display the uterine boundary 810 in the 2D ultrasound image 620. According to another embodiment, the processor 320 may determine the uterine boundary 810 based on a user input received via an input interface, and display the uterine boundary 810 in the 2D ultrasound image 620.

According to an embodiment, the GUI view may show an endometrial boundary 820 in the 2D ultrasound image 620. According to an embodiment, the processor 320 may automatically recognize and display the endometrial boundary 820 in the 2D ultrasound image 620. According to another embodiment, the processor 320 may determine the endometrial boundary 820 based on a user input received via the input interface and display the endometrial boundary 820 in the 2D ultrasound image 620.

According to an embodiment, the GUI view may provide characteristics related to a junction zone surrounding the endometrial boundary 820. For example, the GUI view may provide, on the 2D ultrasound image 620, information 830 about the amount of blood flow in a junction zone.

According to an embodiment, the GUI view may provide a contraction indicator 840 indicating the extent of contraction of the junction zone. The contraction indicator 840 may indicate the extent of contraction of the uterus. A success rate of embryo transfer may be increased by performing the embryo transfer when there is no uterine contraction. According to an embodiment, the contraction indicator 840 may be displayed as a circle and shown in a first color (e.g., green) when contraction is not detected or in a second color (e.g., red) when contraction is detected. According to an embodiment, the processor 320 may acquire information about contraction of the uterus based on the 2D ultrasound image 620. For example, the processor 320 may acquire information about the contraction of the uterus based on movement of at least of the uterine boundary 810 and the endometrial boundary 820 or a combination thereof. According to another embodiment, the processor 320 may receive and acquire information about contraction of the uterus from an external apparatus.

According to an embodiment, the GUI view may provide information about a target position 850. The processor 320 may determine the target position 850 based on the above-described criteria and display an indicator indicating the target position 850 in the 2D ultrasound image 620.

According to an embodiment, the GUI view may provide guide information 860 indicating a direction in which a procedure tool is to move to reach the target position 850. For example, the guide information 860 may be provided in the form of a vector or an arrow indicating a direction in which the procedure tool has to move.

Figure 9:
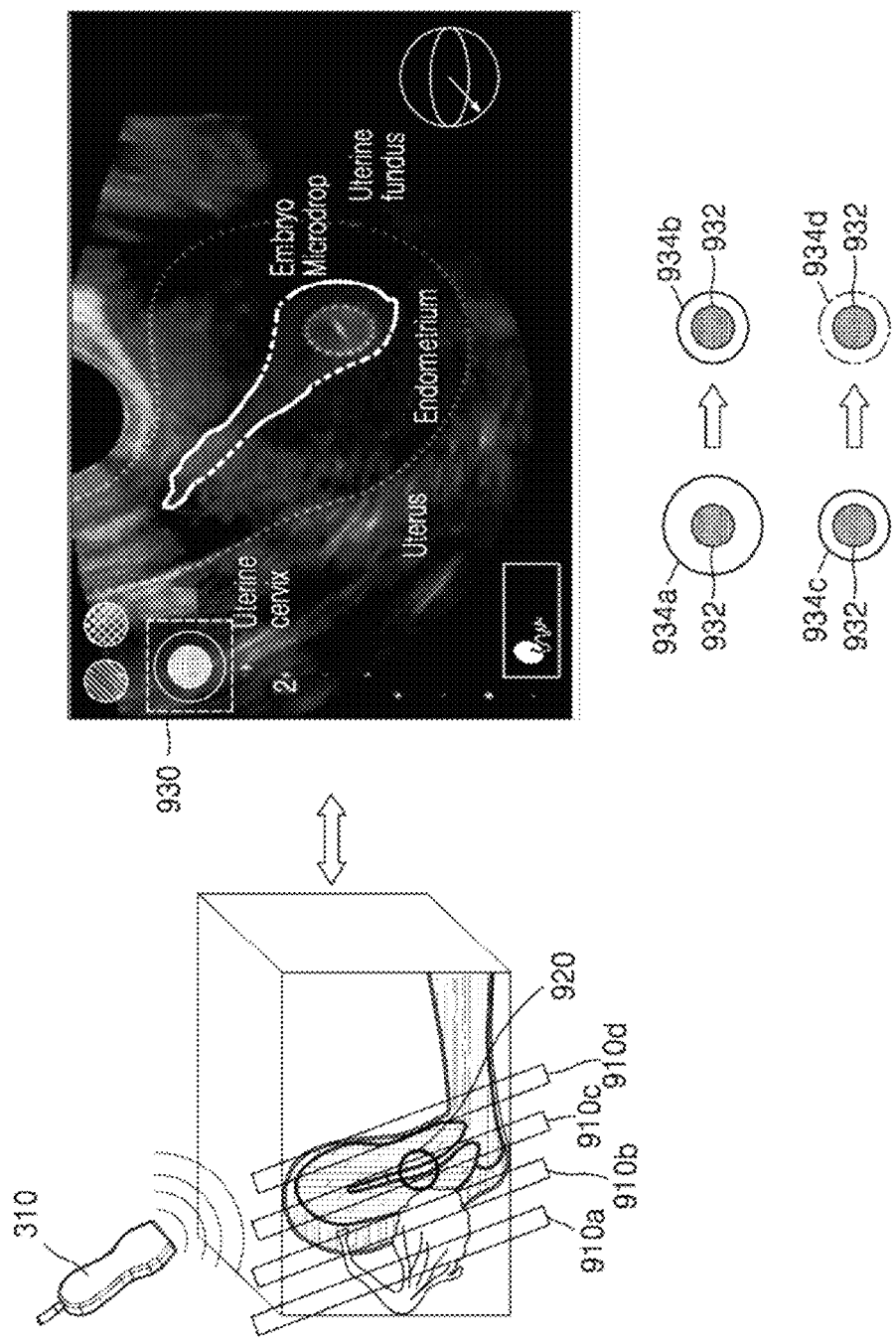
FIG. 9 illustrates a GUI view according to an embodiment.

FIG. 9 illustrates a GUI view according to an embodiment.

According to an embodiment, the GUI view may provide an imaging position indicator 930 indicating information about whether the 2D ultrasound image 620 obtained via the probe 310 is being captured of a target position. The processor 320 may calculate information about a distance between the target position and the 2D ultrasound image 620 being captured and provide the information about the distance via a GUI. For example, when the target position is in a plane corresponding to 910c and the 2D ultrasound image 620 obtained via the probe 310 deviates from the plane corresponding to 910c but is in a plane corresponding to 910a, 910b, or 910d, the target position may not be properly imaged. According to an embodiment, the imaging position indicator 930 may include a first sub-indicator 932 corresponding to a position of a plane corresponding to the target position and second sub-indicators 934a, 934b, 934c, and 934d corresponding to a position of a plane corresponding to the 2D ultrasound image 620 captured by the probe 310. When a plane corresponding to the 2D ultrasound image 620 moves from 910a to 901b to approach 910c including the target position, the second sub-indicator 934a may be changed to the second sub-indicator 934b to indicate that an imaging position corresponding to the 2D ultrasound image 620 is close to the target position. When the plane corresponding to the 2D ultrasound image 620 moves from 910b to 910d to be in a different direction than 910c including the target position, the second sub-indicator 934c may be changed to the second sub-indicator 934d by changing the type of a line of the second sub-indicator 934b.

Figure 10:
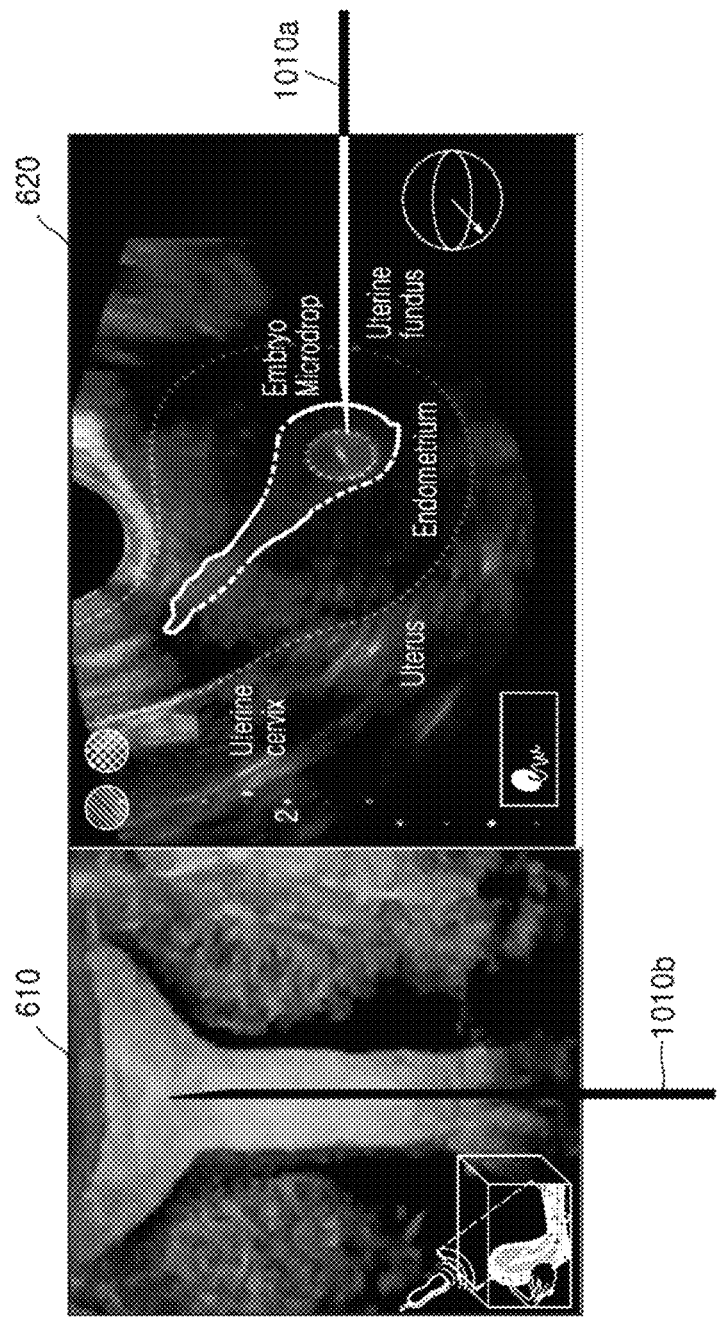
FIG. 10 illustrates a GUI view according to an embodiment.

FIG. 10 illustrates a GUI view according to an embodiment.

According to an embodiment, the GUI view may show a procedure tool indicator 1010a or 1010b indicating a position of a procedure tool. The procedure tool indicator 1010a or 1010b may be displayed in only a 2D ultrasound image 620, only a 3D medical image 610, or both the 2D ultrasound image 620 and the 3D medical image 610. The processor 320 may detect the procedure tool in the 2D ultrasound image 620. The 2D ultrasound image 620 may show the procedure tool being imaged. The processor 320 may provide the procedure tool indicator 1010a by displaying a boundary of the imaged procedure tool in the 2D ultrasound image 620. The processor 320 may determine a position of the procedure tool in the 3D medical image 610 based on the position of the procedure tool detected in the 2D ultrasound image 620 and display the procedure tool indicator 1010b in the 3D medical image 610 based on the determined position of the procedure tool.

Figure 11:
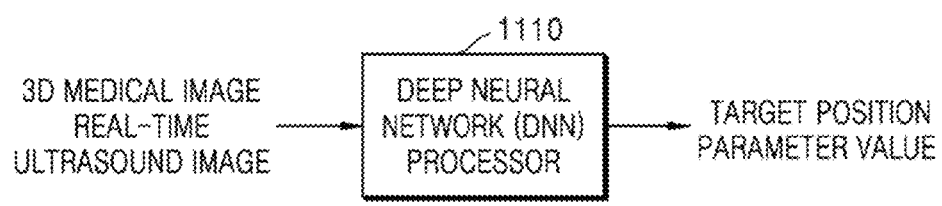
FIG. 11 illustrates a method of determining a target position according to an embodiment.

FIG. 11 illustrates a method of determining a target position according to an embodiment.

According to an embodiment, the processor 320 may determine a target position for embryo transfer based on a 3D medical image by using a deep neural network (DNN) processor 1110. The DNN processor 1110 may be included in the processor 320 or may be provided as a separate processor in the ultrasound imaging apparatus 300 or in an external apparatus such as a server. According to an embodiment, the DNN processor 1110 receives a 3D medical image to output a target position for embryo transfer. According to another embodiment, the DNN processor 1110 may receive a 3D medical image and a 2D ultrasound image. According to another embodiment, the DNN processor 1110 may receive a 3D medical image and additional information (e.g., uterine contraction information) acquired from the external apparatus. According to another embodiment, the DNN processor 1110 may output a target position and at least one parameter value related to embryo transfer.

The DNN processor 1110 may include a pre-trained DNN. For example, the DNN processor 1110 may include a neural network structure such as a convolutional neural network (CNN) or a recurrent neural network (RNN), or a combination of various neural network structures.

Embodiments of the disclosure may be implemented through non-transitory computer-readable recording media having stored thereon computer-executable instructions and data. The instructions may be stored in the form of program code, and when executed by a processor, generate a predetermined program module to perform a specific operation. Furthermore, when being executed by the processor, the instructions may perform specific operations according to the embodiments.

According to embodiments of the disclosure, a success rate of embryo transfer to the uterus may be increased.

Furthermore, according to embodiments of the disclosure, user convenience may be increased and a guide may be provided to the user during embryo transfer to the uterus.

While embodiments of the disclosure have been particularly shown and described with reference to the accompanying drawings, it will be understood by those of ordinary skill in the art that various changes in form and details may be made therein without departing from essential characteristics or the spirit and scope of the disclosure as defined by the appended claims. The disclosed embodiments should be considered in a descriptive sense only and not for purposes of limitation.

What is claimed is:

1. An ultrasound imaging apparatus comprising:
    a probe configured to transmit ultrasound waves and detect echo signals;
    a display; and
    at least one processor configured to generate an ultrasound image based on the echo signals, wherein the at least one processor is further configured to:
        obtain a three-dimensional (3D) medical image of a uterus,
        recognize an anatomical structure of the uterus in the 3D medical image,
        acquire a value of at least one parameter based on the 3D medical image,
        create a 3D transfer probability map including an evaluation value indicating an implantation success rate at each position in the uterus based on the anatomical structure of the uterus and the value of the at least one parameter,
        determine a target position for optimal embryo placement based on the 3D transfer probability map,
        obtain a real-time ultrasound image of the uterus that is a two-dimensional (2D) ultrasound image,
        register the real-time ultrasound image with the 3D medical image,
        determine whether the real-time ultrasound image corresponds to a plane where the target position is included, and
        control the display to display the real-time ultrasound image and an indicator that guides for moving the probe to obtain the real-time ultrasound image corresponding to the plane where the target position is included.

2. The ultrasound imaging apparatus of claim 1, wherein the at least one processor is further configured to match the value of the at least one parameter acquired based on the 3D medical image to the real-time ultrasound image, and control the display to display information about the value of the at least one parameter in the real-time ultrasound image.

3. The ultrasound imaging apparatus of claim 1, wherein the at least one parameter comprises at least one of an endometrial thickness, a blood flow amount, a junction zone location, a uterine boundary location, an endometrial location, a myoma location, and an adenomyoma location, or a combination thereof.

4. The ultrasound imaging apparatus of claim 1, wherein the probe comprises at least one sensor including at least one of a position sensor, a gyro sensor, and an accelerometer, and
    wherein the at least one processor is further configured to register the 3D medical image with the real-time ultrasound image based on a signal detected by the at least one sensor.

5. The ultrasound imaging apparatus of claim 1, wherein the at least one processor is further configured to control the display to display an indicator representing a position of a plane corresponding to the real-time ultrasound image with respect to the 3D medical image.

6. The ultrasound imaging apparatus of claim 1, wherein the 3D medical image and the real-time ultrasound image are respectively obtained by apparatuses using different imaging modalities.

7. The ultrasound imaging apparatus of claim 1, wherein the at least one processor is further configured to control the display to display information about the evaluation value at a position of at least a portion of the uterus.

8. The ultrasound imaging apparatus of claim 1, wherein the at least one processor is further configured to control the display to display an indicator representing a distance between a plane corresponding to the real-time ultrasound image and the plane where target position is included.

9. The ultrasound imaging apparatus of claim 1, wherein the real-time ultrasound image shows at least one procedure tool inserted into the uterus, and
    wherein the at least one processor is further configured to control the display to display the 3D medical image and the real-time ultrasound image and provide, on the 3D ultrasound image, information about a position of the at least one procedure tool detected in the real-time ultrasound image.

* * * * *